United States Patent [19]
Goodwin, Jr.

[11] Patent Number: 5,284,753
[45] Date of Patent: * Feb. 8, 1994

[54] MULTIPLE-SITE CHEMOTACTIC TEST APPARATUS AND METHOD

[75] Inventor: Rchard H. Goodwin, Jr., Bethesda, Md.

[73] Assignee: Neuro Probe, Inc., Cabin John, Md.

[ * ] Notice: The portion of the term of this patent subsequent to May 11, 2010 has been disclaimed.

[21] Appl. No.: 4,944

[22] Filed: Jan. 15, 1993

Related U.S. Application Data

[63] Continuation-in-part of Ser. No. 672,561, Mar. 20, 1991, Pat. No. 5,210,021.

[51] Int. Cl.⁵ .................. C12Q 1/02; C12Q 1/24; C12M 3/00
[52] U.S. Cl. .................. 435/30; 435/29; 435/284; 435/285; 435/291; 435/310; 435/311
[58] Field of Search ............... 435/284, 285, 291, 310, 435/311, 29, 30

[56] References Cited

U.S. PATENT DOCUMENTS

| | | | |
|---|---|---|---|
| 3,888,770 | 6/1975 | Avital et al. | 210/238 |
| 3,929,583 | 12/1975 | Sharpe et al. | 435/301 |
| 4,317,726 | 3/1982 | Shepel | 210/236 |
| 4,493,815 | 1/1985 | Fernwood et al. | 422/101 |
| 4,514,495 | 4/1985 | Schalkowsky et al. | 435/32 |
| 4,714,674 | 12/1987 | Palladino | 435/18 |
| 4,912,057 | 3/1990 | Guirguis et al. | 435/285 |
| 5,023,173 | 6/1991 | Horwitz et al. | 435/29 |

OTHER PUBLICATIONS

W. Falk, R. H. Goodwin, Jr. and E. J. Leonard, "A 48-Well Micro Chemotaxis Assembly for Rapid and Accurate Measurement of Leukocyte Migration," Journal of Immunological Methods, 33, pp. 239-247 (1980).
L. Harvath, W. Falk and E. J. Leonard, "Rapid Quantitation of Neutrophil Chemotaxis: Use of a Polyvinylpyrrolidone-Free Polycarbonate Membrane in a Multiwell Assembly," Journal of Immunological Methods, 37, pp. 39-45 (1980).
K. L. Richards and J. McCullough, "A Modified Mirocochamber Method for Chemotaxis and Chemokinesis," Immunological Communications, 13(1), pp. 49-62 (1984).
W. L. Falk, L. Harvath and E. J. Leonard, "Only the Chemotactic Subpopulation of Human Blood Monocytes Expresses Receptors for the Chemotactic Peptide N-Formylmethionyl-Leucyl-Phenylalanine," Infection and Immunity, pp. 450-454 (May 1982).
L. Harvath and E. J. Leonard, "Two Neutrophil Populations in Human Blood with Different Chemotactic Activities: Separation and Chemoattractant Binding," Infection and Immunity, pp. 443-449 (May 1982).
"Neuro Probe 48 Well Micro Chemotaxis Chamber Manual," (1980).
Neuro Probe, Inc. Sales Brochure, "48 Well Micro Chemotaxis Chamber", 1988.
Neuro Probe, Inc. Sales Brochure, "12 Well Chemotaxis Chamber", 1988.

(List continued on next page.)

Primary Examiner—Robert J. Warden
Assistant Examiner—Krisanne M. Thornton
Attorney, Agent, or Firm—Kirkland & Ellis

[57] ABSTRACT

A simple chemotaxis apparatus and method wherein surface tension, capillary action, and hydrophobic forces are used to hold cell suspensions, chemotactic factors, and control fluids in place on both membrane filters and chemotaxis plates. In one embodiment, chemotactic factors and controls are placed at preselected areas on the top surface of a bottom plate, while a membrane filter topped with cell suspensions is placed above the bottom plate so that the drops of chemotactic factors and controls contact the filter membrane directly below the locations of the cell suspensions. In another embodiment, the preselected locations on the bottom plate are rimmed wells that are filled with chemotactic factors and controls. Hydrophobic coating is used to limit fluid movement on the filter membrane and on the bottom plate. Occluding materials or monolayers of cells are used to further limit the gravitational fluid flow in the preferred embodiments.

40 Claims, 8 Drawing Sheets

OTHER PUBLICATIONS

Neuro Probe, Inc. Sales Brochure, "12 Well Manifold Chamber", 1988.
Neuro Probe, Inc. Sales Brochure, "10 Well Chemotaxis Chamber", 1988.
Neuro Probe, Inc. Sales Brochure, "Blind Well and Boyden Chambers", 1988.
Neuro Probe, Inc. Sales Brochure, "Single Well and Four Well Separation Chambers", 1988.
Neuro Probe, Inc. Sales Brochure, "Three Tiered Chamber", 1988.
Neuro Probe, Inc. Sales Brochure, "Zigmond Chamber", 1988.
Neuro Probe, Inc. Sales Brochure, "Guirguis Chamber"; 1988.
Neuro Probe, Inc. Sales Brochure, "Accessories", 1988.

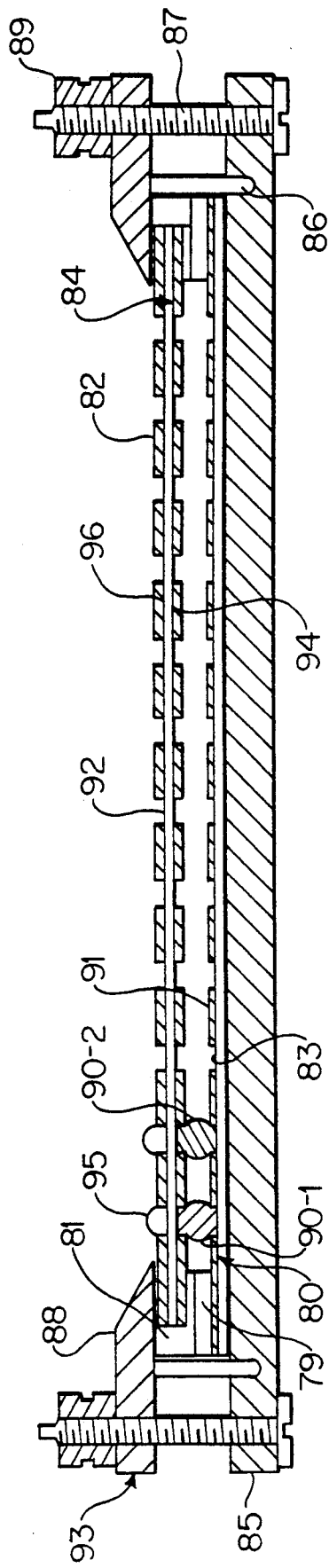
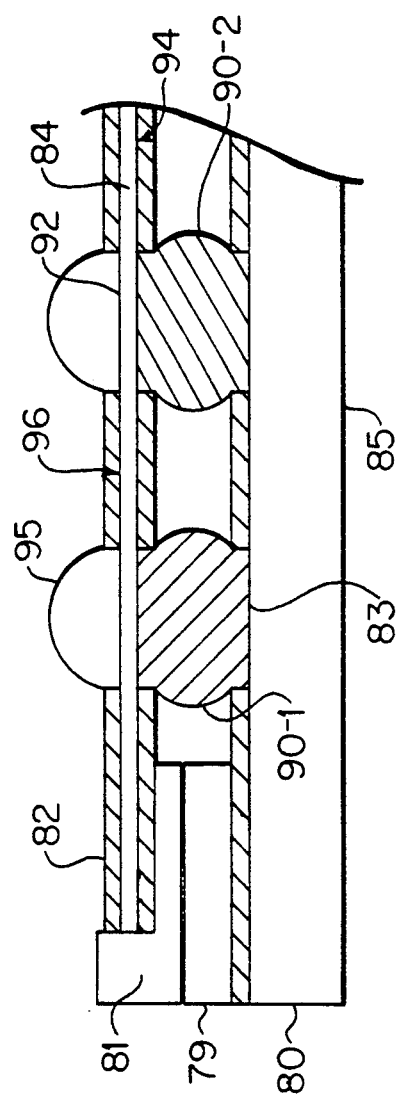
FIG. 11a
FIG. 11b

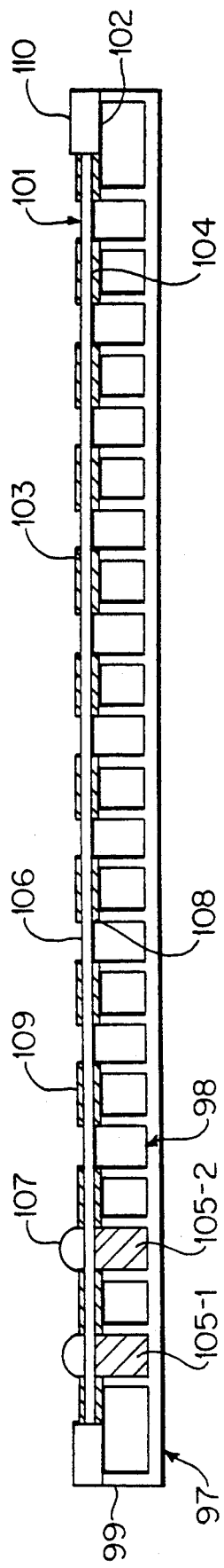
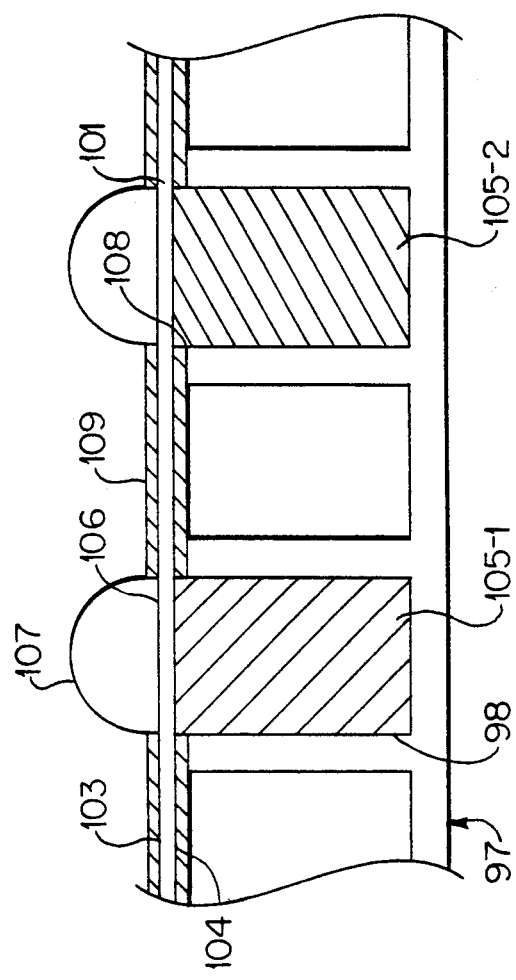
FIG. 12b
FIG. 12c

MULTIPLE-SITE CHEMOTACTIC TEST APPARATUS AND METHOD

The present application is a continuation-in-part of application Ser. No. 07/672,561, filed on Mar. 20, 1991 now U.S. Pat. No. 5,210,021 ("the parent application"), which is expressly incorporated by reference herein.

BACKGROUND

Field of the Invention

The present invention relates to chemotaxis chambers, i.e., to chambers for measuring the effect of concentration gradients of mobile chemicals upon the directional response of biological cells. More specifically, the present invention relates to chemotaxis test sites comprising top and bottom regions separated by one or more membrane filters.

Background of the Invention

Chemotaxis is the directional response of biological cells or organisms to concentration gradients of mobile chemicals. Conventional chemotaxis chambers comprise two compartments separated by a filter, with one or both of the compartments open to air. Cells in suspension are placed in the upper compartment, and a chemotactic factor or control is placed in the bottom compartment. The chemotactic factor can be used in various dilutions to get a dose-response curve. The controls are generally of two kinds: negative, when the same medium is used to suspend the cells above and below the filter; and chemokinetic, when a chemotactic factor is placed in the same concentration in the medium with the cells and on the opposite side of the filter. Chemokinetic controls allow the user to distinguish heightened random activity of the cells, due to contact with the chemotactic factor, from directional response in a concentration gradient of the chemotactic factor.

Chemotactic activity is measured by first establishing a stable concentration gradient in the chemotaxis chamber. The chamber is incubated for a predetermined time, then the filter is removed from the apparatus. The cells that have migrated through the filter (or into the filter to a certain depth) are then counted. A comparison is then made between the activity of the cells in a concentration gradient of the chemotactic factor being tested, and the activity of the cells in the absence of the concentration gradient.

The apparatus can also be used to measure the response of cells of different origins—e.g., immune cells from patients suffering from diseases—to a chemotactic factor of known chemotactic activity. In this case the cells in question are challenged by both a negative control and the chemotactic factor to see if the differential response is depressed or normal.

Microchemotaxis chambers and some of their applications are described in Falk, et al., "A 48 Well Micro Chemotaxis Assembly for Rapid and Accurate Measurement of Leukocyte Migration," *Journal of Immunological Methods*, 33, 239–247 (1980); Harvath, et al., "Rapid Quantification of Neutrophil Chemotaxis: Use of a Polyvinylpyrrolidone-free Polycarbonate Membrane in a Multiwell Assembly," *Journal of Immunological Methods*, 37, 39–45 (1980); Richards, et al., "A Modified Microchamber Method for Chemotaxis and Chemokinesis," *Immunological Communications*, 13 (1), 49–62 (1984); Falk, et al., "Only the Chemotactic Subpopulation of Human Blood Monocytes Expresses Receptors for the Chemotactic Peptide N-Formylmethionyl-Leucyl-Phenylalanine," *Infection and Immunity*, 36, 450–454 (1982); and Harvath, et al., "Two Neutrophil Populations in Human Blood with Different Chemotactic Activities: Separation and Chemoattractant Binding," *Infection and Immunity*, 36 (2), 443–449 (1982), all of which are hereby expressly incorporated by reference herein.

SUMMARY OF THE INVENTION

The present invention is a multiple-site chemotaxis test apparatus comprising a membrane filter having areas which hold the fluid on the top and bottom of the filter by surface tension.

In some embodiments of the present invention, the membrane filter is a capillary pore membrane. The pores in the capillary pore membrane filter are between 0.1 and 14 microns in diameter, depending on the type of cell which is being used in the assay, and the nature of the assay. For example, a 0.1 or 0.2 micron pore size can be used to allow the pseudopods of certain cells (e.g., cancer cells) to penetrate the membrane in response to a chemotactic factor, but preclude the cell bodies from getting through the membrane. The differential response is then measured by determining how much the pseudopods protrude in stimulated as opposed to unstimulated "wells." However, if very large cells are used, and the assay is read by counting migrated cells, then the pores must be large enough for those cells to migrate through the pores.

Initially, the fluid on top of the filter is comprised of cells suspended in media (i.e., cells in a balanced salt and nutrient solution), and the fluid on the bottom of the filter is either just media (a negative control) or a solution of chemotactic factor and media. Chemokinetic controls, however, contain the same concentration of chemotactic factor above and below the filter (i.e., chemokinetic controls differ from the chemotaxis test sites because there is no gradient in the concentration of the chemotactic factor). In its simplest form, the test apparatus consists of a sheet of membrane filter, typically 6 to 30 microns thick, attached to a rigid frame. The pores in the membrane are usually chosen to be between 2 and 14 microns. However, when cell bodies must be prevented from migrating, smaller pore sizes are used. Drops of chemotactic factor and drops of control solution(s) are placed on one side of the filter in a well-defined pattern, e.g., 96 spots, 9 mm apart in a 12×8 array. The filter and frame are then turned over, and drops of a cell suspension are pipetted onto the other side, on spots corresponding to the initial placement of the chemotactic factors and control solution(s). The drops can range in volume from 2 to 75 μl. The drops of fluid are held in place by surface tension. Gravity induces top-to-bottom flow after fluid is placed on both sides of the filter until the surface tension forces of the bottom drop equal the gravitational and surface tension forces of the top drop. The apparatus is then incubated at 37°±1° C., for periods ranging from 15 minutes to 72 hours.

When the framed filter is removed from the incubator, several different protocols can be followed, depending on whether one or two filters are employed, and what type or types of filters are used. One protocol appropriate to an apparatus comprising a single capillary pore membrane filter is to remove the cells from the non-migrated side of the filter and then fix, stain and count the cells that have migrated through the filter.

Another protocol is to fix all the cells and then count the ones that have migrated. In either method, the migrated cells are counted on the bottom side of each exposed filter area and a comparison is made between the activity of the cells exposed to the chemotactic factor and the activity of the cells exposed to the controls. If a non-capillary pore membrane is used, such as a cellulose nitrate filter, then the distance the cells have travelled into the filter matrix, i.e., the distance between the leading front of migrating cells in the filter matrix and their starting point on the surface of the filter is measured. If two filters are used, the top filter is discarded and the cells on the bottom filter are counted. Cells can also be labelled with a radioisotope such as $Cr^{51}$, and then the amount of radioactivity can be measured at each site of the bottom filter, after discarding the top filter.

Many different stains and staining techniques can be used, including, for example, fluorescent stains.

Further embodiments of the invention discussed herein incorporate features for stabilizing concentration gradients at the sites where chemotactic factors or controls and cell suspensions are placed on the filter by blocking or inhibiting gravity-driven flow of the fluids through the filter at those sites.

A first object of the present invention is to provide a simple apparatus and method for the measurement of the chemotactic activity of a plurality of specimens.

A further object of the present invention is to provide an inexpensive and/or disposable multiple-site chemotaxis test apparatus.

A further object of the present invention is to provide a multiple-site chemotaxis test apparatus requiring very small volumes of cell suspension for the precise measurement of chemotactic factor activity.

An additional object of the present invention is to provide a high sensitivity multiple-site chemotaxis test apparatus.

A further object of the present invention is to provide a chemotaxis test apparatus that can be analyzed using an automatic microtiter plate reader.

BRIEF DESCRIPTION OF THE DRAWINGS

FIGS. 11a-11c are schematic representations of a twelfth embodiment of the present invention showing an apparatus comprised of an upper filter component and a bottom plate component, separated by a spacer and held together by a clamping apparatus.

FIGS. 12a-12c are schematic representations of a thirteenth embodiment of the present invention showing an apparatus comprised of an upper filter component and a bottom plate component having a large number of wells.

DETAILED DESCRIPTION OF THE INVENTION

Figure 1:
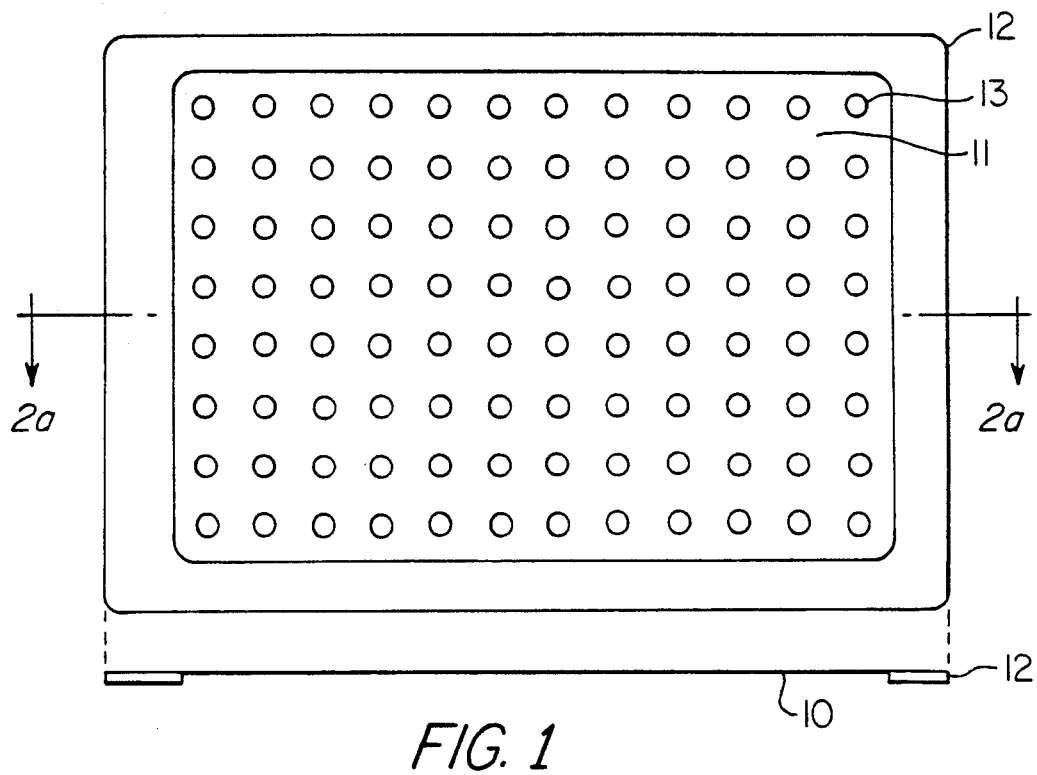
FIG. 1 is a schematic representation of a first embodiment of the chemotaxis apparatus of the present invention.

In its simplest embodiment, shown in FIG. 1, the multiple-site chemotaxis test apparatus 10 of the present invention comprises a membrane filter 11 (e.g., a 10 $\mu$m thick polycarbonate capillary pore membrane filter with 5 $\mu$m holes manufactured by Poretics (Livermore, Cal.) or Costar Nuclepore (Pleasanton, Cal.)) attached to a rigid frame 12, as shown in FIG. 1. The terms "test site" or "site" are used herein to refer to a delineated spot on a filter where a solution of chemotactic factor or plain media is positioned, and juxtaposed thereto, on the opposite side of the filter, a suspension of cells is positioned, whether these fluids are kept in position by compartments, as in conventional chemotaxis chambers, or by surface tension. The position of the chemotaxis test sites is defined by, for example, a pattern 13 on filter 11. The pattern, which identifies the locations of the chemotaxis test sites, may be formed by ink imprinted on the filter, may be a patterned film of plastic or silicone, or may be defined by a patterned hydrophobic coating silk-screened or otherwise applied to the filter. In this first preferred embodiment of the present invention, the chemotactic fluids are kept in position by surface tension. The frame can be plastic, stainless steel, aluminum, or another suitable material. The frame must be rigid enough to keep the filter and any grids attached thereto flat. The membrane filters can be attached to the frame by any suitable fastening means, including glue, heat seals, ultrasonic seals, or mechanical means.

Figure 2A:
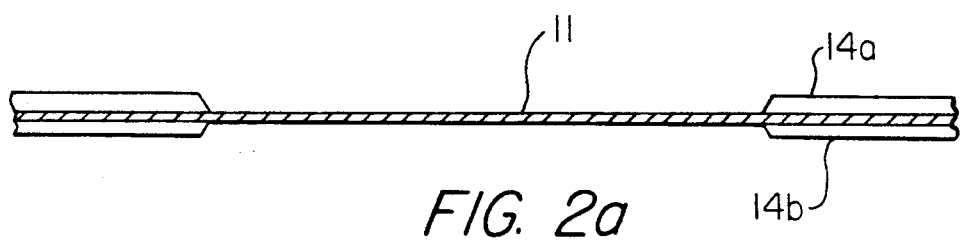
FIGS. 2a-2d are enlarged views of a portion of the chemotaxis apparatus of the present invention, showing a single chemotaxis test site, at different stages of the procedure.
Figure 2B:
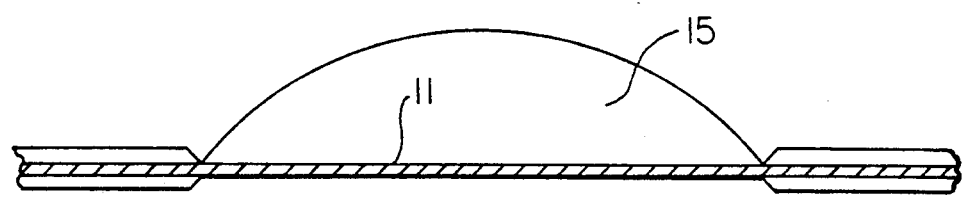
Figure 2C:
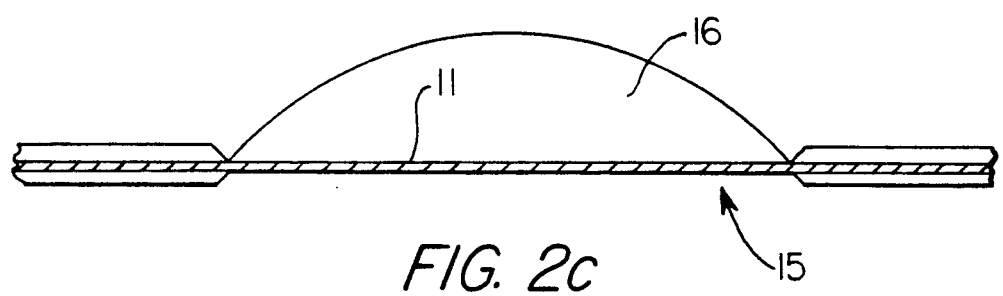
Figure 2D:
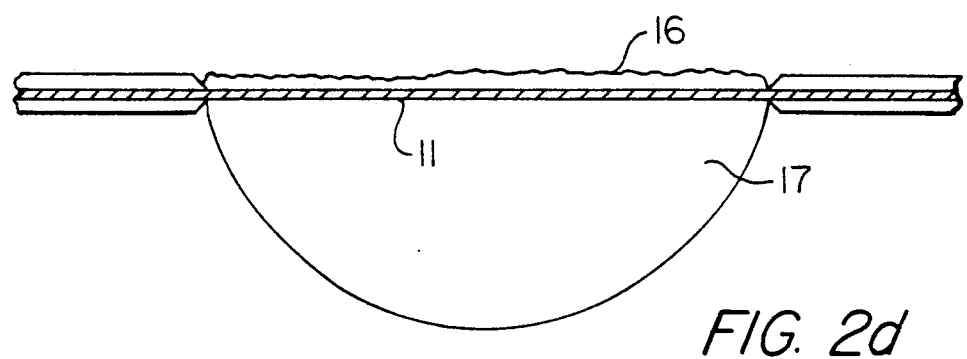

FIGS. 2a-2d are enlarged views of a portion of the chemotaxis apparatus, showing a single chemotaxis test site at successive stages of the procedure. In the embodiment shown in FIGS. 2a-2d, the pattern on filter 11 is formed by hydrophobic coatings 14a on the top side and 14b on the bottom side of filter 11. The hydrophobic coatings cover the entire filter, except at the locations defining the chemotaxis test sites. In this instance, fluid transport through the filter is only possible at these locations. FIG. 2a shows the chemotaxis test site before the addition of any fluids. FIG. 2b shows the chemotaxis test site after the addition of the chemotactic factor or control 15. FIG. 2c shows the chemotaxis test site after the chemotaxis apparatus has been turned over, and a cell suspension 16 has been added to the other side of filter 11 at locations opposite to the chemotactic factor or control 15 on the first side, before the fluid has stabilized. FIG. 2d shows the chemotaxis test site after the fluids have stabilized, when the gravitational and surface tension forces have been equalled by the surface tension forces. In FIG. 2d, the fluid 17 on the bottom side of filter 11 now includes media that has flowed to that side of the filter from the cell suspension on the opposite side of the filter.

The apparatus is used according to the following procedure. Drops of various control solutions and drops of chemotactic factor (sometimes at varying concentrations) are placed on one side of the membrane filter in a well-defined pattern delineated by printing on or otherwise applied to the surface of the membrane, or by silk-screening or depositing a coating on the membrane. The coating may simply define the locations of the chemotaxis test sites, or it may also function as a hydrophobic barrier, spatially restricting the chemotactic fluid. The apparatus is then turned over, and the cell suspension is pipetted onto the corresponding test sites on the opposite side. In some embodiments, gravity and surface tension induce flow from the cell-suspension side of the membrane to the opposite side until these forces come into equilibrium. In other embodiments, surface tension and capillary action forces prevent gravity-induced flow.

The apparatus is then incubated (usually at 37° C.) for a predetermined time period, typically in the range of 15 minutes to 72 hours, depending upon the nature of the cells, the membrane filter used, the chemotactic factors being tested, etc. After incubation, cells that have not migrated from the cell-suspension side of the filter are usually removed by one of several techniques including those utilizing squeegees, wiper blades and cotton swabs. This procedure is repeated after immersing the filter in a phosphate-buffered saline solution between wipings. If a double filter barrier is used, the filter with the non-migrated cells is usually discarded. Sometimes, however, the non-migrated cells are not removed, allowing them to be studied or counted as well as the migrated cells. For example, cells on one side of a polycarbonate capillary pore membrane filter 10 microns thick can be examined and counted using confocal microscopy without visual interference by the cells on the opposite side of the membrane.

The cells in or on the filter are then fixed (e.g., about 2 minutes in methanol) and allowed to dry (sometimes the filter is mounted on a glass slide, and dried). The cells on the mounted filter are then stained, if necessary (e.g., with DiffQuik®, manufactured by Baxter-Dade, Miami, Fla.). The number of cells that have migrated through or into the filter in each test site are then counted. The cells can be counted individually using a microscope (e.g., with a 25× objective), or the number of cells could be estimated using specialized equipment such as an optical density reader (e.g., a UVmax Model optical density reader manufactured by Molecular Devices, Menlo Park, Cal. or by Optomax Image Analyzer manufactured by Optomax, Inc., Hollis, N.H.). If the cells are labeled with a radioactive isotope, the test sites are separated from each other and cells are counted using a scintillation counter (e.g., Packard Instrument Co., Downers Grove, Ill.).

When this first embodiment of the apparatus of the present invention is used, obtaining the proper placement of the drops on the membrane filter can be accomplished with a hand-held pipette, an automatic variable-volume pipette, or an automatic pipetting machine. As shown in FIG. 1, the spacing and position of the drops of chemotactic fluid, i.e., the position of the individual chemotaxis test sites, is indicated by pattern 13. The position and spacing of the 96 chemotaxis test sites is preferably a standard spacing, e.g., the standard spacing for 96-well microtiter plates, and the outside dimensions of the frame are preferably identical to the dimensions of standard microtiter plates, so that automatic equipment such as the UVmax optical density reader can be used for counting cells.

Figure 3A:
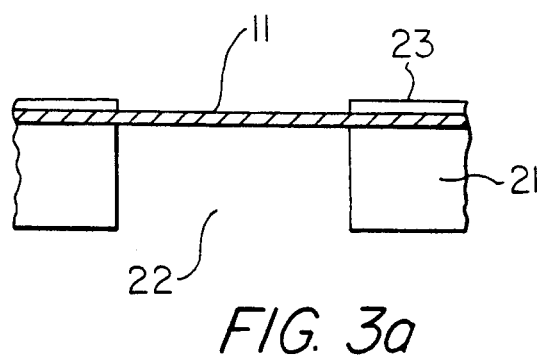
FIGS. 3a-3d are schematic representations of a second embodiment of the present invention showing the use of a grid positioned below the filter.
Figure 3B:
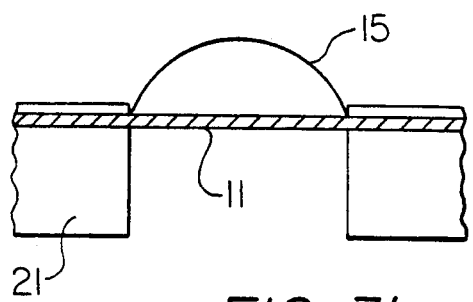
Figure 3C:
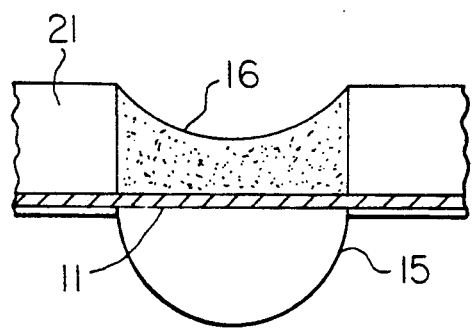
Figure 3D:
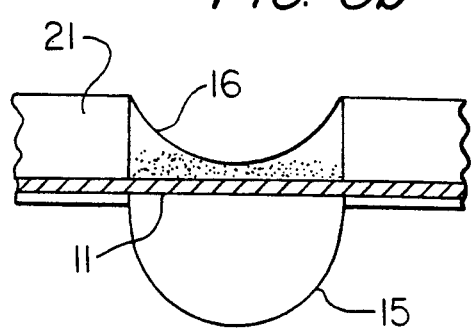

In a second preferred embodiment of the present invention, shown schematically in FIGS. 3a-3d, the apparatus also includes a grid 21 containing an array of holes 22. FIG. 3a also shows an optional patterned hydrophobic coating 23 on filter 11. FIG. 3b shows the apparatus after chemotactic factor or control 15 has been added. FIGS. 3c and 3d show the apparatus after it has been turned over, and a cell suspension 16 has been added. FIG. 3c shows the initial disposition of cell suspension 16, and FIG. 3d shows the disposition of cell suspension 16 after it has stabilized, when the gravitational and surface tension forces from above the filter are equalled by surface tension forces from below the filter.

Grid 21 may be manufactured from any rigid or flexible material that is not biologically active or water-soluble, e.g., plastics such as acrylic, polystyrene, polycarbonate, polyethylene, or polypropylene; silicone; or metals such as coated aluminum, steel, or stainless steel. In this embodiment, for example, the holes may be placed in a 9 mm center-to-center pattern composed of 12 rows and 8 columns—the standard microtiter configuration. They may be arranged in any convenient pattern, however, on smaller or larger frames with a greater or lesser number of test sites. For example, when the final counting will be done using a microscope, the test sites could be arranged on a smaller frame, e.g., 2"×3" in a pattern closer than the 9 mm center-to-center pattern of the standard microtiter plate. In this preferred embodiment, the holes can vary in diameter from 0.5 mm to 7 mm. The optimum grid thickness depends upon the diameter of the holes, and the material of the grid. If the grid material is hydrophilic (or possibly if the grid material is neither hydrophilic nor hydrophobic) and the holes are 1 mm in diameter, the grid could be 0.5 mm thick. Capillary forces would then hold a large proportion of the fluid above the filter, as shown in FIG. 3d. If the grid material is hydrophobic, then the fluid may all be forced through the filter, as shown in FIG. 2d. If the wells were 6 mm in diameter and the grid material were hydrophilic or neutral, the grid material should be thicker to hold enough fluid above the filter to allow the concentration gradient of the chemotactic factor to develop.

Figure 4A:
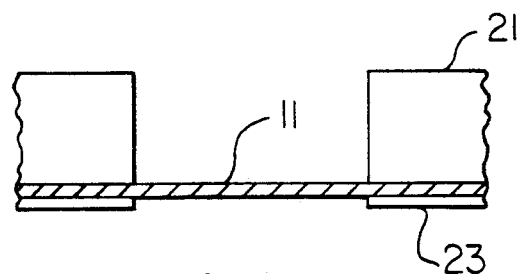
FIGS. 4a-4d are schematic representations of a third embodiment of the present invention showing the use of a grid positioned above the filter.
Figure 4B:
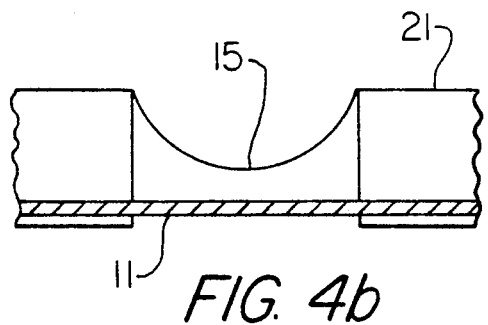
Figure 4C:
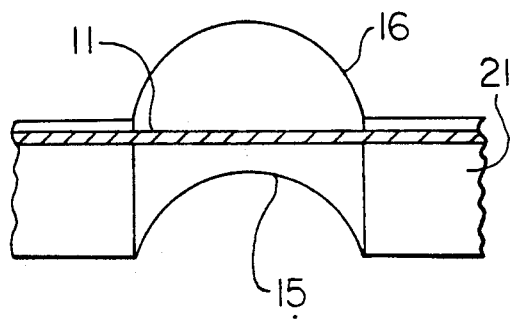
Figure 4D:
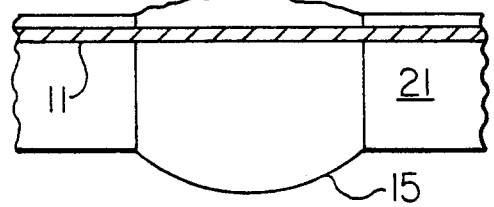

In a third preferred embodiment of the present invention, shown in FIGS. 4a-4d, filter 11 is attached to the bottom of grid 21. FIG. 4a shows an optional patterned hydrophobic coating 23 on filter 11. FIGS. 4a-4d show the disposition of the chemotactic fluid 15 (FIGS. 4b, 4c and 4d) and cell suspension 16 (FIG. 4c and 4d). FIG. 4c shows the disposition of the fluids immediately after the cell suspension is added, and FIG. 4d shows the disposition of the fluids after stabilization.

Figure 5A:
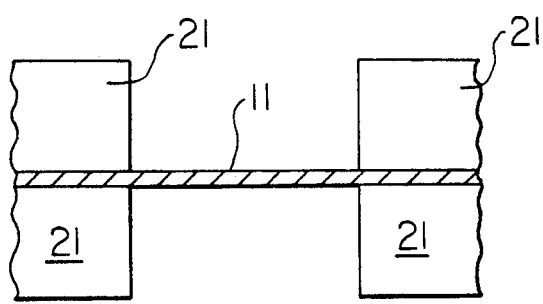
FIGS. 5a-5d are schematic representations of a fourth embodiment of the present invention showing the use of grids positioned both below and above the filter.
Figure 5B:
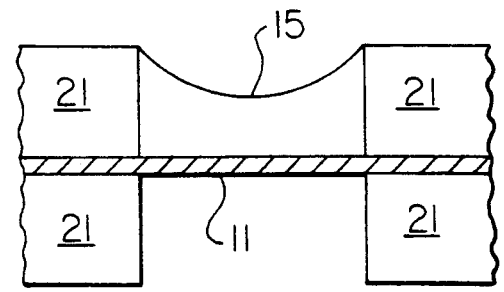
Figure 5C:
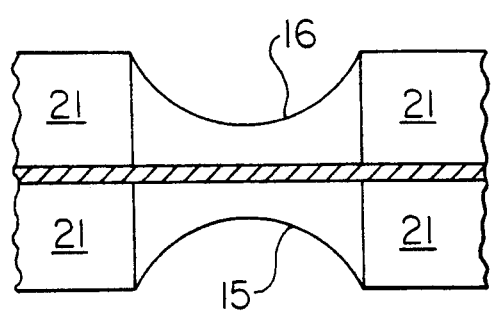
Figure 5D:
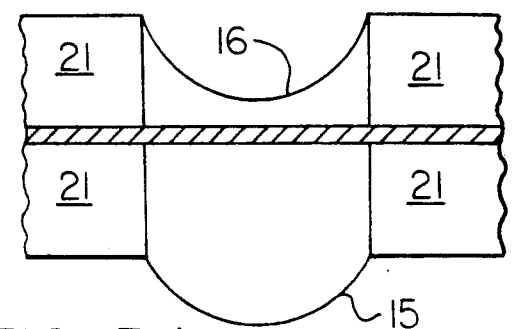

In a fourth preferred embodiment of the present invention, two grids are used, as shown in FIGS. 5a-5d. One grid 21 is attached to the top of filter 11, and one grid 21 is attached to the bottom of filter 11. Chemotactic factors or controls 15 are added to one side of filter 11, as shown in FIG. 5b, and cell suspensions 16 are added to the other side of filter 11, as shown in FIG. 5c. FIG. 5c shows the disposition of the cell suspension initially. FIG. 5d shows the disposition of the fluids after stabilization.

Figure 6:
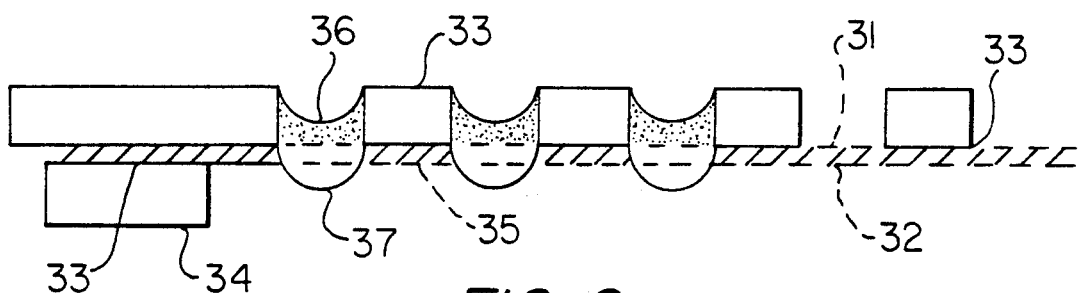
FIG. 6 is a schematic representation of a fifth embodiment of the present invention showing an apparatus constructed from two filters bonded to each other with a removable seal.

A fifth preferred embodiment of the present invention uses two capillary pore membrane filters 31 and 32, as shown in FIG. 6, or one capillary pore membrane and one non-capillary pore membrane, or two non-capillary pore membranes. Filters 31 and 32 are each permanently bonded to grid 33 and outer frame 34, respectively. Filters 31 and 32 face each other, and are in direct contact with each other. FIG. 6 shows a gap between filters 31 and 32 only to make FIG. 6 more easily understood. The filters are temporarily bonded to each other by means of, for example, a thin pressure-sensitive adhesive seal 35. The filters are sealed around each chemotaxis test site where cell suspensions 36, and controls and chemotactic factors 37 are to be positioned.

The chemotactic activity of the chemotactic factors is then determined according to the following procedure. First, the chemotaxis apparatus is inverted and chemotactic factors and controls 37 are placed on filter 32 opposite to the openings in grid 33. Second, the apparatus is placed right side up, and cell suspensions 36 are placed on filter 31 within the openings in grid 33. Capillary action will hold most of the fluid in the top compartment, at which point a concentration gradient of the chemotactic factor will be established in those test sites containing chemotactic factors. Third, the apparatus is placed in an incubator. Fourth, the apparatus is removed from the incubator after incubation at about 37° C. for a period of time (between 30 minutes to 72 hours). The cells are then fixed, and the top grid and filter are separated from the bottom frame and filter. Fifth, the bottom filter is stained. Finally, the number of cells on the bottom filter is counted.

Depending on both the kind of filter employed for the bottom filter and the counting technique used (optical, densitometry, etc.), different methods would be used to handle the bottom filter after its separation from the top filter. For example, if a capillary pore polycarbonate filter is to be used as the bottom filter, the filters can be separated before or after fixing and the cells and/or cellular debris on the top side of the bottom filter can be removed or not removed. If a standard optical technique is to be used to count the cells attached to the bottom filter, it may be desirable to remove cells and cellular debris from the top surface of the bottom filter.

Figure 7:
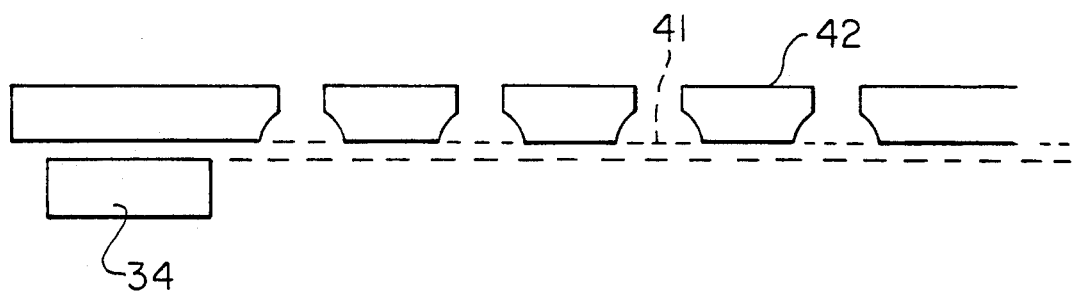
FIG. 7 is a schematic representation of a sixth embodiment of the present invention that utilizes specially shaped holes in a grid to control gravity flow.

A sixth preferred embodiment of the present invention, shown in FIG. 7, uses the same structure as the fifth embodiment, i.e., two membrane filters 41, the first mounted on grid 42, the second mounted to frame 34. Grid 42 and frame 34 are attached to each other so that the two filters 41 are in direct contact with one another. However, in this embodiment, the holes in the grids are specially shaped to increase the amount of fluid held by capillary action in the top portion of each chemotaxis test site after fluid stabilization. For example, as shown in FIG. 7, the opening of each hole in grid 42 is relatively narrow, with the diameter of the hole increasing towards filters 41.

Figure 8A:
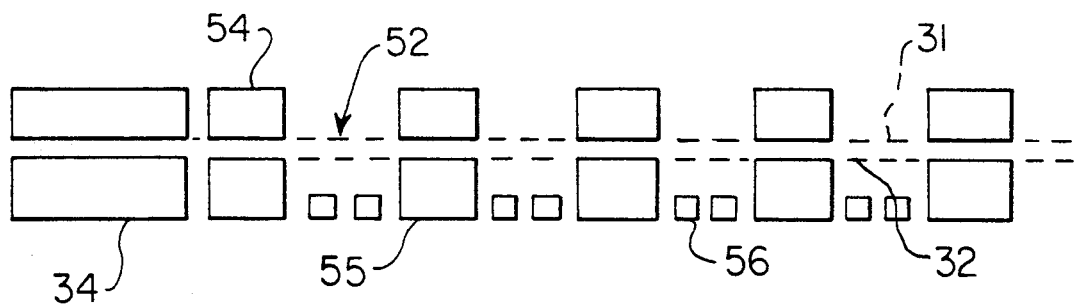
FIGS. 8a-8b are schematic representations of a seventh embodiment of the present invention incorporating specially shaped holes in a grid to control gravity flow.
Figure 8B:
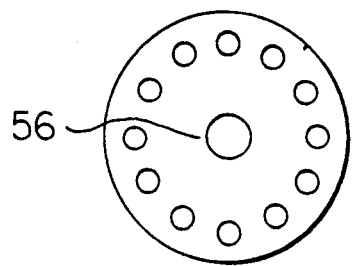

A seventh preferred embodiment is shown in FIGS. 8a and 8b. This embodiment is similar to the sixth embodiment, but top grid 54 comprises relatively large holes 52, whereas bottom grid 55 comprises numerous smaller holes 56 corresponding to each larger hole 52 in top grid 54. FIG. 8a shows a cross-section of the apparatus viewed from the side. FIG. 8b is a view of one test site from the bottom of bottom grid 55, showing the disposition of small diameter holes 56 in bottom grid 55. The small diameter holes provide larger capillary action forces, counteracting the effect of gravitational and surface tension forces on the fluids above. An alternative to this embodiment comprises one grid with small holes that preclude gravity flow on the chemotactic factor side of the filters (usually the bottom side) and a hydrophobic coating (but no deep grid) on the cell suspension side (usually the top side). This configuration allows a drop of cell suspension to sit on top of a flat filter and not flow through at all (or very little), so that the concentration gradient is established immediately. Because there is plenty of fluid with the cells, the concentration gradient does not disappear rapidly. Also, the top surface can be easily wiped clean of cells that have not migrated.

An eighth preferred embodiment of the present invention also uses the same structure as the fifth embodiment, i.e., two capillary pore membrane filters mounted on grids which are attached to each other such that the filters are in direct contact with each other. In this embodiment, a flexible pressure-sensitive sheet is used to seal off one side of a grid after its compartments are filled, or partially filled. The sheet limits gravity-induced flow when fluid is added to the other side of the filter, thus establishing a stable concentration gradient.

Figure 9A:
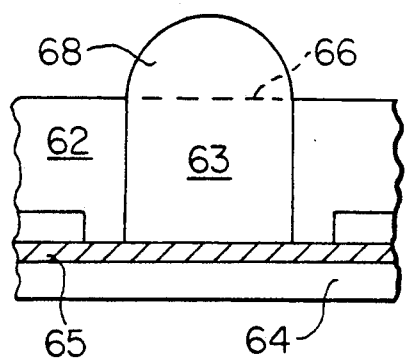
FIGS. 9a-9b are schematic representations of a ninth embodiment of the present invention incorporating a pressure-sensitive adhesive-backed sheet.
Figure 9B:
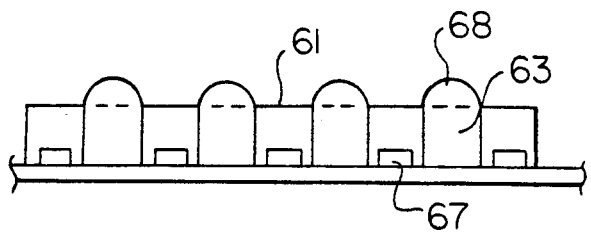

A ninth preferred embodiment of the present invention is similar to the eighth embodiment, but uses a single filter, as shown in FIGS. 9a-9b. This embodiment is used by filling the test sites formed by holes 61 in grid 62 with cell suspensions 63. A sheet 64 backed with a pressure-sensitive adhesive 65 is applied to the side of grid 62 opposite to filter 66. Excess cell suspension is expressed and trapped in the recesses 67 between the test sites, and the apparatus is inverted. Chemotactic factor 68 is then pipetted onto the opposite side of the filter 66 over each of the wells. The apparatus is then inverted again and incubated. Since the top wells of the test sites are sealed, the media in which the cells are suspended cannot flow through the filter upsetting the concentration gradient. Another way to use this apparatus would be to put the chemotactic factor(s) and control(s) in the side to be sealed, then pipette the cell suspension onto the opposite side.

Figure 10A:
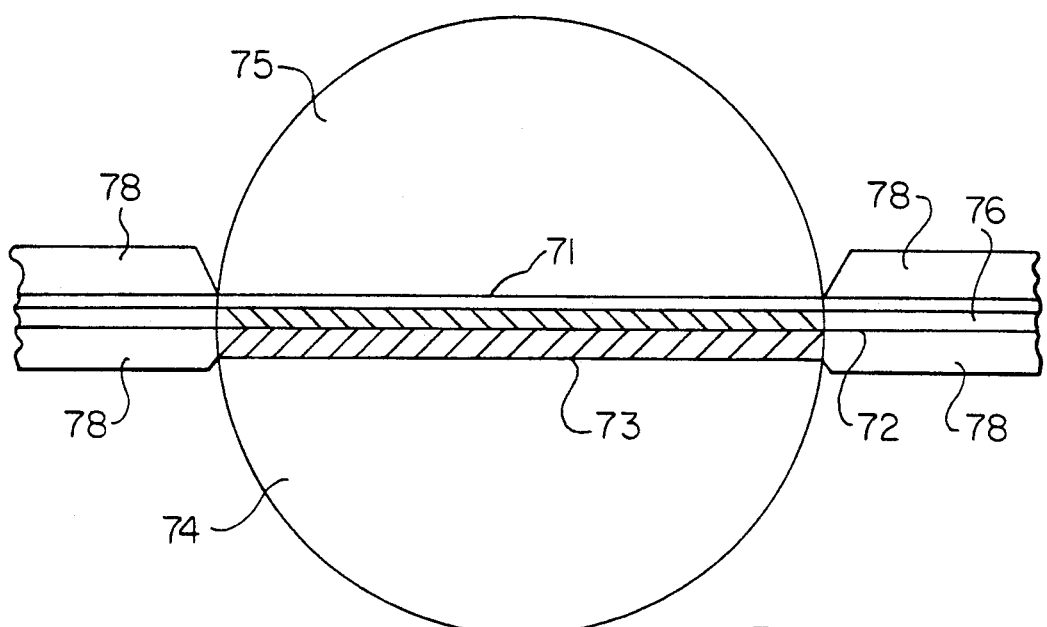
FIGS. 10a-10b are schematic representations of a tenth embodiment of the present invention incorporating a material that blocks fluid flow but allows diffusion of chemotactic factors and migration of cells.
Figure 10B:
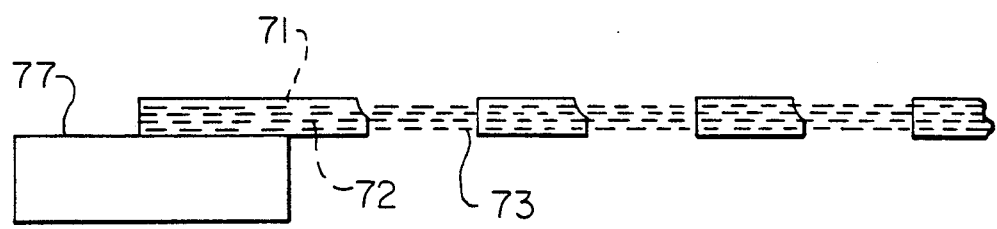

A tenth preferred embodiment of the present invention, which can use either two filters (as in the eighth preferred embodiment) or a single filter (as in the ninth preferred embodiment) is shown in FIGS. 10a-10b (two filter version). FIG. 10a is a cross-sectional side view of an individual chemotaxis test site. FIG. 10b is a cross-sectional side view of several chemotaxis test sites. FIG. 10a shows a top filter 71 and a bottom filter 72 placed close together facing each other, separated by a small space (5-20 $\mu$m). The pores of the filter(s) and any space between the filters (if two filters are used) are filled with an occluding material 73 such as agar or Matrigel ® (available from Becton Dickinson Collaborative Biomedical Products, Bedford, Mass.) that will allow diffusion of chemotactic factors 74 and migration of the cells in cell suspension 75, and will not dissolve in media (or will dissolve slowly enough to allow the assay to be completed). The two filters are kept close together by a removable pressure-sensitive adhesive 76 that surrounds each test site. The assembly is supported by an outer frame 77, as shown in FIG. 10b. The apparatus is similar to the apparatus of the eighth preferred embodiment (if two filters are used) or to the ninth preferred embodiment (if a single filter is used). Gravity does not affect the fluids since the agar (or equivalent occluding material) prevents the vertical flow of the fluids. If two filters are used, capillary pore filters are preferred since melted agar will flow between the two filters by capillary action, leaving no voids. Horizontal flow is prevented by a relatively hydrophobic coating 78 surrounding each test site.

In an eleventh preferred embodiment of the present invention, the two-filter structure disclosed in the fifth embodiment is used, but the pressure-sensitive adhesive is soluble in a solvent such as ethanol that does not dissolve the filters. The two filters could then be easily separated after the apparatus is soaked in, for example, ethanol fixative. Alternatively, the top filter could be made from a material (e.g., cellulose nitrate) that dissolves in a solvent (e.g., ethanol), and the bottom filter could be made from a material (e.g., polycarbonate) that does not dissolve in that solvent. The top filter would then be dissolved in the solvent after the cells are fixed, or during the fixing process. In either alternative, after the bottom filter is separated from the top filter, the bottom filter would be stained and the number of cells on or in the bottom filter would be determined using any of the techniques discussed above.

Figure 11C:
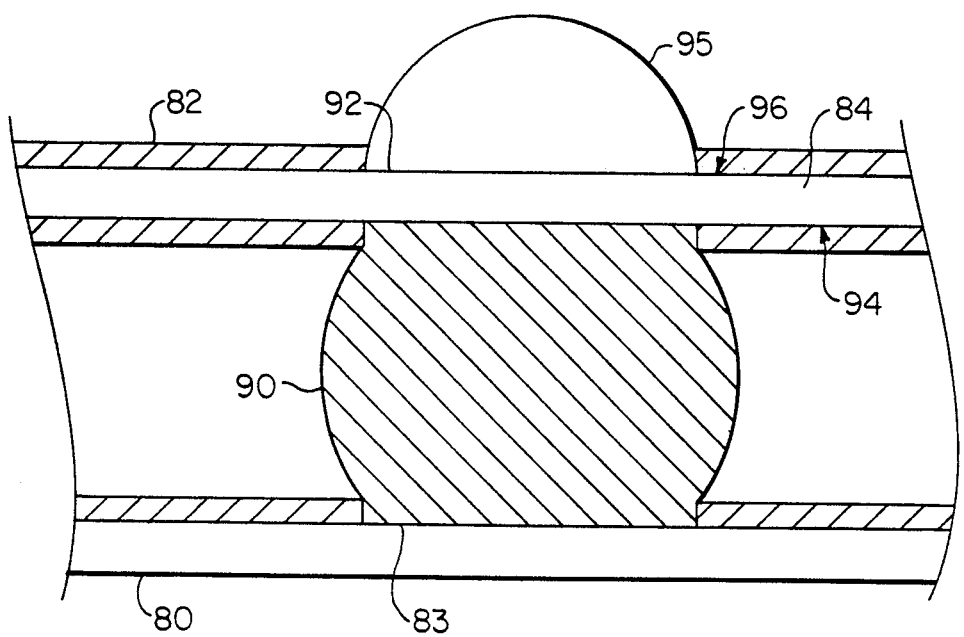

A twelfth preferred embodiment of the present invention is shown in FIGS. 11a–11c. In this embodiment, as shown in FIG. 11a, the apparatus includes a spacer 79 and a bottom plate 80. The spacer 79 is the same shape as the filter frame 81 of the filter 84 and can be between 0.02 and 0.2 inches thick. Bottom plate 80 may be manufactured from any clear rigid material that is not biologically active or water-soluble, e.g., glass, sapphire, acrylic, polystyrene, polycarbonate. The bottom plate 80 has a hydrophobic coating 82 applied to its top surface 91, except at a number of uncoated sites 83. These uncoated sites 83 are circular and can vary in diameter from 0.04 to 0.5 inches. One typical pattern of sites is the microtiter plate configuration as described in the first embodiment of the present invention.

The upper component of this embodiment includes a filter 84 surrounded by filter frame 81, wherein the top surface 96 of filter 84 and the bottom surface 94 of filter 84 are covered with a patterned hydrophobic coating 82, as described in the first preferred embodiment of the present invention and as shown in FIG. 1. Hydrophobic coating 82 is patterned to create a number of uncoated filter sites 92 corresponding to uncoated sites 83 on bottom plate 80. FIG. 11a also shows a clamping apparatus 93 comprising a support plate 85 with positioning pins 86, bolt 87, and a clamping plate 88 with thumb nuts 89.

Bottom plate 80, spacer 79, and filter frame 81 are all aligned by the positioning pins 86 and are clamped between the support plate 85 and the clamping plate 88 through the action of the thumb nuts 89 on the bolt 87. FIGS. 11a–11c show chemotactic factor 90-1 (or control solution 90-2) trapped between the uncoated sites 83 of the bottom plate 80 and the uncoated filter sites 92 of filter 84. As shown in FIG. 11b, the hydrophobic coating 82 on bottom plate 80 and the hydrophobic coating 82 on the bottom surface 94 of the filter prevent the chemotactic factor 90-1 (or the control solution 90-2) from spreading and making contact with fluid at nearby sites. Cell suspension 95 is placed on the uncoated filter sites 92 of the top surface 96 of the filter 84. Hydrophobic coating 82 on the top surface 96 of the filter 84 surrounding the uncoated filter sites 92 prevents the drops of cell suspension 95 from moving across the membrane and contacting one another.

FIG. 11c is an enlarged view of one chemotactic test site of this embodiment. When the surface tension of the drop of chemotactic factor 90-1 (or control solution 90-2) equals the sum of the surface tension on the drop of cell suspension 95 and the force of gravity, the two drops are in equilibrium and no flow occurs through the filter 84. The volumes of these drops, the surface area of each uncoated filter site 92 and the surface area of each uncoated site 83 on the bottom plate 80, and the surface tension properties of the fluid determine whether there will be flow through the uncoated filter sites 92 of the filter 84 when the cell suspension 95 is pipetted onto those uncoated filter sites 92.

In practice, it is necessary to have an initial flow of about 10% of the volume of each drop of cell suspension 95 downward through each uncoated filter site 92. This insures that an optimum concentration gradient of the chemotactic factor 90-1 (or the control solution 90-2) will form when the surface tension and gravitational forces reach equilibrium. If the flow is upward, however, the chemotactic factor 90-1 (or the control solution 90-2) flows into the cell suspension 95 before equilibrium is achieved, and the cell suspension 95 is contaminated with chemotactic factor 90-1 (or control solution 90-2). In such a case, the chemotactic factor 90-1 (or control solution 90-2) either binds to the cells in a random (non-directional) manner and prevents the cells from exhibiting a chemotactic response or attenuates the chemotactic response if the upward flow is small.

In the twelfth embodiment, cell suspensions 95 can be placed on the uncoated filter sites 92 before or after filter 84 is placed into clamping apparatus 93.

The uncoated filter sites 92 can also be coated with occluding material as in embodiment 10 or the sites can have monolayers of cells cultured on them which occlude the pores of the filter. In either of these two cases, there will be no flow between the top surface 96 and bottom surface 94 of the filter 84 after it is placed over the bottom plate 80 and the drops of chemotactic factor 90-1 (or control solution 90-2) make contact with the underside of the filter sites 92.

Figure 12A:
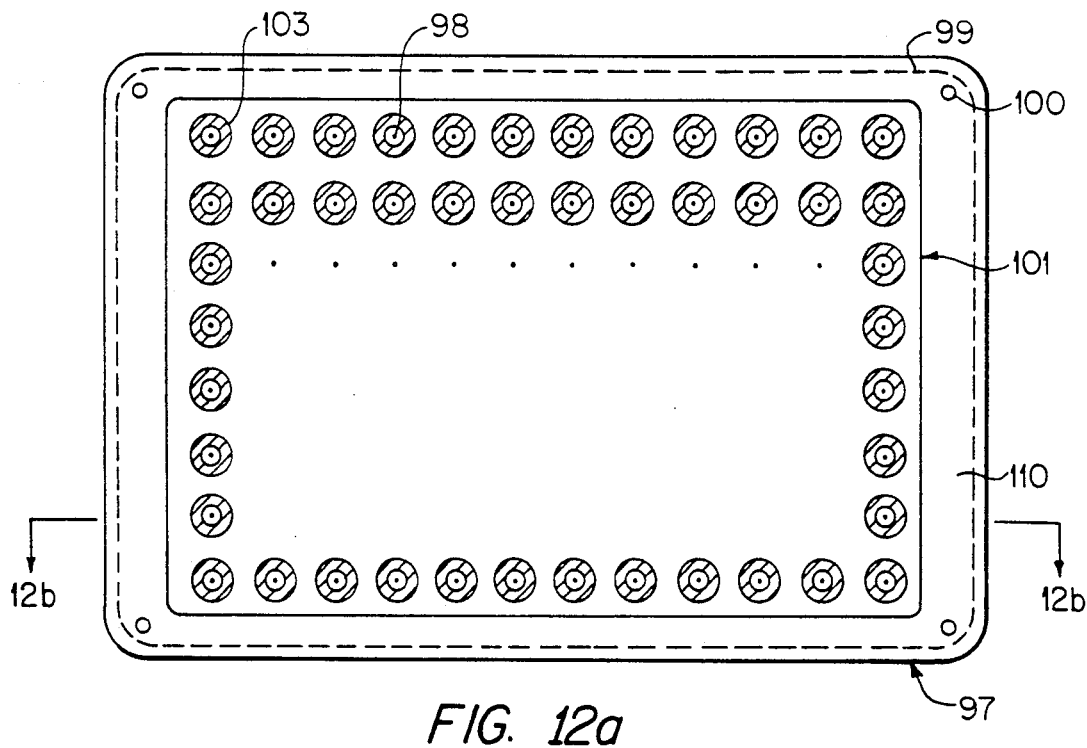

A thirteenth preferred embodiment of the present invention is shown in FIGS. 12a–12c. In this embodiment, the apparatus includes a bottom plate 97 with ninety-six wells 98, a rim 99 running around the perimeter of the bottom plate 97, four reference pins 100, and an overlaying filter 101 surrounded by a filter frame 110. FIG. 12b is a cross-sectional view of this embodiment taken along line A—A, with the filter frame 110 and the filter 101 secured on top of the bottom plate 97 with a layer of pressure-sensitive adhesive 102. FIG. 12c is an enlargement of a portion of FIG. 12b showing two chemotaxis test sites.

In FIG. 12a, the filter frame 110 with the attached filter 101 is positioned over the bottom plate 97 so that the rim 99 of the bottom plate 97 is under the filter frame 110 of the filter 101. Bottom plate 97 may be manufactured from any clear rigid material that is not biologically active or water-soluble, e.g., glass, sapphire, acrylic, polystyrene, polycarbonate. The bottom plate 97 has a large number of wells 98 (in this case, ninety-six) with diameters between 0.04 and 0.5 inches. One typical pattern of sites is the microtiter plate configuration as described in the first embodiment of the present invention.

As shown in FIGS. 12b and 12c, the upper component of this embodiment includes the filter 101 surrounded by an attached filter frame 110, wherein the top surface 103 and the bottom surface 104 of the filter 101 are partially covered with a patterned hydrophobic coating 109. The hydrophobic coating 109 is patterned to create a number of uncoated filter test sites 106 corresponding to the location of the wells 98 in the bottom plate 97. FIG. 12a also shows how the bottom plate 97 and the framed filter 101 are aligned by the positioning pins 100.

FIGS. 12b and 12c show chemotactic factor 105-1 (or control solution 105-2) trapped in the wells 98 of the bottom plate 97 by the bottom surface of the uncoated filter test sites 106 and the hydrophobic coating 109 on the bottom surface 104 of the framed filter 101. The hydrophobic coating 109 on the bottom surface 104 of the framed filter 101 touches or nearly touches (less than 0.01 inch) the well rims 108 of the bottom plate 97. The hydrophobic coating 109 surrounding the uncoated filter test sites 106 on the bottom surface 104 of the filter 101 and touching or in close proximity to the well rims 108 prevents the chemotactic factor 105-1 (or control solution 105-2) from wicking (by capillary action) between the well rims 108 and the framed filter 101. When a drop of cell suspension 107 is pipetted onto the top surface 103 of the framed filter 101 at the uncoated filter sites 106, the fluid in the cell suspension 107 is prevented from flowing through the filter and into the wells 98, as there is no unfilled volume therein (i.e.. the wells 98 are completely filled with chemotactic factor 105-1 (or control solution 105-2) and that fluid is trapped by the walls of the wells 98, and the hydrophobic coating 109 surrounding the uncoated filter test sites 106). Likewise, the hydrophobic coating 109 on the top surface 103 of the filter 101 surrounding the uncoated filter test sites 106 prevents the drops of cell suspension 107 from moving outside the perimeter of the test sites and contacting each other.

With this thirteenth embodiment, the fluid in the cell suspension 107 has no initial flow through the uncoated filter sites 106 (unlike the twelfth embodiment). No downward flow of the fluid of the cell suspension 107 is possible because the volume under the uncoated filter test sites 106 is completely filled by the chemotactic factor 105-1 (or control solution 105-2) in the wells 98. On the other hand, if excess chemotactic factor 105-1 (or control solution 105-2) is pipetted into the wells 98 of the bottom plate 97, it is squeezed out when the framed filter 101 is positioned over and bonded to the bottom plate 97 with the pressure-sensitive adhesive 102, leaving completely filled wells 98.

The uncoated filter test sites 106 can also be coated with a semipermeable occluding material, such as Matrigel ® (Becton Dickinson Collaborative Biomedical Products, Bedford, Mass.), as in embodiments ten and twelve, or the sites can have monolayers of cells cultured on them which occlude the pores of the filter. These conditions allow the investigation of cell migration through other cell layers or through other materials. In neither of these cases, nor in the case where there is no occluding substance in the pores of the filter, will there be a flow of the cell suspension 107 through the filter 101 after it is placed over the bottom plate 97 and the drops of chemotactic factor 105-1 (or control solution 105-2) in the wells 98 make contact with the bottom surface 104 of the filter 101. In the former two cases, the cell suspension 107 does not flow downward due to the occlusion of the pores in the filter, while in the latter case, there is no flow simply because there is no volume under the filter test site 106 into which the cell suspension 107 can flow. Additionally, as long as the wells 98 are completely filled, the exact amount of chemotactic factor 105-1 (or control solution 105-2) pipetted into each well 98 is not critical to the uniformity of the experimental conditions, as it is in the twelfth embodiment.

After an incubation period, the cells on the top surface of the uncoated filter sites 106 can be removed with their suspending media, thereby leaving the migrated cells on the bottom of the filter, in the pores of the filter, or in the wells 98 of the bottom plate 97. At this time, the assembled chemotaxis apparatus can be spun in a centrifuge or the cells on the filter 101 can be pretreated with various solutions (familiar to those practiced in the art) to facilitate their detachment during centrifugation. The migrated cells can then be prepared in various ways familiar to those practiced in the art and counted in automatic cell counting machines. The cells can also be counted directly on the filter 101, either in an automatic machine (e.g., Millipore's CytoFluor ®) or under a microscope, by removing the framed filter 101 from the bottom plate 97. The bottom plate 97 can also be read by itself after removing the framed filter without centrifugation to count any cells that have fallen off the filter.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for performing chemotaxis tests, comprising:
    (a) providing at least one bottom plate having a top side with a perimeter and a bottom side;
    (b) placing drops of chemotactic factor at a first set of preselected locations on the top side of said at least one bottom plate;
    (c) placing drops of controls at a second set of preselected locations on the top side of said at least one bottom plate;
    (d) placing at least one framed membrane filter having a top side and a bottom side over the top side of said at least one bottom plate, such that the drops of chemotactic factor and the drops of controls contact the bottom side of said at least one framed membrane filter;
    (e) placing drops of cell suspensions on the top side of said at least one framed membrane filter at preselected filter locations directly above the first and second sets of preselected locations on the top side of said at least one bottom plate;
    (f) incubating said at least one framed membrane filter for a period of time at least sufficient to allow the surface tension forces to come into equilibrium with gravitational forces, thereby establishing a chemotactic factor concentration gradient; and (g) determining the response of cell suspension to the chemotactic factor concentration gradient and the controls.

2. The method of claim 1, wherein said first and second sets of preselected locations on the top side of said at least one bottom plate comprise a pattern defining the positions of said first and second set of preselected locations.

3. The method of claim 2, wherein the pattern is formed by applying a hydrophobic coating on the top side of said at least one bottom plate.

4. The method of claim 2, further comprising placing a spacer of predetermined height having a top side and a bottom side on top of the perimeter of the top side of said at least one bottom plate, such that said spacer is sandwiched between the perimeter of the top side of said at least one bottom plate and the bottom side of the frame of said framed membrane filter, leaving a space between the bottom side of said framed membrane filter and the top side of said bottom plate equal to the height of said spacer and trapping therebetween said drops of chemotactic factor and controls.

5. The method of claim 4, wherein said at least one bottom plate, said spacer, and said at least one framed membrane filter are held in place with a clamping apparatus.

6. The method of claim 5, wherein said clamping apparatus aligns said at least one bottom plate, said spacer, and said at least one framed membrane filter by means of at least one positioning pin.

7. The method of claim 5, wherein said drops of cell suspension are placed on the top side of said at least one framed membrane filter before said clamping apparatus is attached.

8. The method of claim 5, wherein said drops of cell suspension are placed on the top side of said at least one framed membrane filter after said clamping apparatus is attached.

9. The method of claim 2, wherein the top and bottom sides of said at least one framed membrane filter include a pattern defining the positions of the preselected filter locations.

10. The method of claim 9, wherein the pattern is formed by applying a hydrophobic coating on the top and bottom sides of said at least one framed membrane filter.

11. The method of claim 2, wherein the preselected filter locations of said at least one framed membrane filter further comprise a coating of an occluding material.

12. The method of claim 2, wherein the preselected filter locations of said at least one framed membrane filter further comprise a monolayer of cultured cells.

13. The method of claim 1, wherein said first and second sets of preselected locations on the top side of said at least one bottom plate comprise first and second predetermined sets of rimmed wells.

14. The method of claim 13, further comprising:
(a) placing the drops of chemotactic factor in the first predetermined set of rimmed wells such that the fluid reaches or exceeds the rims of said rimmed wells;
(b) placing drops of controls in the second predetermined set of rimmed wells such that the fluid reaches or exceeds the rims of said rimmed wells;
(c) placing said at least one framed membrane filter over the rimmed wells of said at least one bottom plate, such that the position of the rims of said rimmed wells approximate the bottom side of said at least one framed membrane filter; and
(d) placing the drops of cell suspensions on the top side of said at least one framed membrane filter at the preselected filter locations directly above the rimmed wells of said at least one bottom plate.

15. The method of claim 14, wherein said at least one bottom plate has at least one upwardly-protruding reference pin and said at least one framed membrane filter has at least one corresponding reference hole, such that the rimmed wells of said at least one bottom plate are positioned directly below the preselected filter locations of said at least one framed membrane filter when the membrane filter is placed on the bottom plate and the upwardly-protruding reference pin engages the corresponding reference hole.

16. The method of claim 14, wherein the bottom side of the frame of said at least one framed membrane filter is bonded to the perimeter of the top side of said at least one bottom plate by a pressure-sensitive adhesive.

17. The method of claim 14, wherein the rimmed wells of said at least one bottom plate are in a microtiter plate configuration.

18. The method of claim 14, wherein said at least one bottom plate comprises 96 rimmed wells.

19. The method of claim 14, wherein the top and bottom sides of said at least one framed membrane filter include a pattern defining the positions of the preselected filter locations.

20. The method of claim 19, wherein the pattern is formed by applying a hydrophobic coating on the top and bottom sides of said at least one framed membrane filter.

21. The method of claim 14, wherein the preselected filter locations of said at least one framed membrane filter further comprise a coating of an occluding material.

22. The method of claim 14, wherein the preselected filter locations of said at least one framed membrane filter further comprise a monolayer of cultured cells.

23. A chemotaxis apparatus comprising:
(a) at least one bottom plate having a top side with a perimeter and a first and second set of preselected locations;
(b) drops of chemotactic factor located at the first set of preselected locations on the top side of said at least one bottom plate;
(c) drops of controls located at the second set of preselected locations on the top side of said at least one bottom plate;
(d) at least one framed membrane filter having a top side and a bottom side and having a pattern on the top and bottom sides of the membrane filter defining the position of a set of preselected filter locations directly above the first and second set of preselected locations on the top side of said at least one bottom plate, said at least one framed membrane filter positioned on top of the top side of said at least one bottom plate, such that the drops of chemotactic factor and the drops of controls contact the bottom side of said at least one framed membrane filter; and
(e) drops of cell suspensions located on the top side of said at least one framed membrane filter at said set of preselected locations.

24. The chemotaxis apparatus of claim 23, wherein said first and second sets of preselected locations on the top side of said at least one bottom plate comprise a pattern defining the positions of said first and second sets of preselected locations.

25. The chemotaxis apparatus of claim 24, wherein the pattern on the top side of said at least one bottom plate comprises an applied hydrophobic coating.

26. The chemotaxis apparatus of claim 24, further comprising a spacer, said spacer being sandwiched between the perimeter of the top side of said at least one bottom plate and the bottom side of the frame of said at least one framed membrane filter, leaving a space between the bottom side of said at least one framed membrane filter and the top side of said bottom plate equal to the height of said spacer and trapping therebetween said drops of chemotactic factor and controls.

27. The chemotaxis apparatus of claim 26, further comprising a clamping apparatus, whereby the said at least one bottom plate, said spacer, and said at least one framed membrane filter are held in place.

28. The chemotaxis apparatus of claim 27, wherein said clamping apparatus further comprises:
   (a) a support plate;
   (b) a clamping plate;
   (c) at least one threaded bolt upwardly disposed through said support plate and said clamping plate and anchored at the bottom surface of said at least one bottom plate;
   (d) at least one reciprocally-threaded thumbnut, whereby said clamping apparatus can be tightened about said at least one bottom plate, said spacer, and said at least one framed membrane filter; and
   (e) at least one positioning pin upwardly-protruding from the top surface of said support plate.

29. The chemotaxis apparatus of claim 24, wherein the pattern on the top and bottom sides of said at least one framed membrane filter comprises an applied hydrophobic coating.

30. The chemotaxis apparatus of claim 24, wherein the preselected filter locations of said at least one framed membrane filter further comprise a coating of an occluding material.

31. The chemotaxis apparatus of claim 24, wherein the preselected filter locations of said at least one framed membrane filter further comprise a monolayer of cultured cells.

32. The chemotaxis apparatus of claim 23, wherein said first and second set of preselected locations on the top side of said at least one bottom plate comprise a first and second predetermined set of rimmed wells.

33. The chemotaxis apparatus of claim 32, further comprising:
   (a) drops of chemotactic factor located in the first predetermined set of rimmed wells, wherein the fluid of said chemotactic factor reaches or exceeds the rims of said rimmed wells;
   (b) drops of controls located in the second predetermined set of rimmed wells, wherein the fluid of said controls reaches or exceeds the rims of said rimmed wells; and
   (c) said patterned framed membrane filter positioned over the rimmed wells of said at least one bottom plate, whereby the rims of said rimmed wells approximate the bottom side of said at least one framed membrane filter.

34. The chemotaxis apparatus of claim 33, further comprising:
   (a) at least one reference pin upwardly protruding from the perimeter of said at least one bottom plate; and
   (b) at least one corresponding reference hole in the frame of said at least one framed membrane filter, whereby said at least one framed membrane filter is held in place atop said at least one bottom plate and said preselected filter locations on said at least one framed membrane filter are aligned vertically with the rimmed wells of said at least one bottom plate.

35. The chemotaxis apparatus of claim 33, further comprising a layer of pressure-sensitive adhesive disposed between the bottom side of the frame of said at least one framed membrane filter and the top side of said at least one bottom plate.

36. The chemotaxis apparatus of claim 33, wherein said bottom plate comprises 96 rimmed wells.

37. The chemotaxis apparatus of claim 33, wherein said bottom plate comprises a microtiter plate configuration.

38. The chemotaxis apparatus of claim 33, wherein the pattern comprises an applied hydrophobic coating on the top and bottom sides of said at least one framed membrane filter.

39. The chemotaxis apparatus of claim 33, wherein the preselected filter locations of said at least one framed membrane filter further comprise a coating of an occluding material.

40. The chemotaxis apparatus of claim 33, wherein the preselected filter locations of said at least one framed membrane filter further comprise a monolayer of cultured cells.

* * * * *